(12) United States Patent
Raz et al.

(10) Patent No.: US 10,605,660 B2
(45) Date of Patent: Mar. 31, 2020

(54) SPECTRAL IMAGING METHOD AND SYSTEM

(71) Applicant: Technology innovation momentum fund (Israel) limited partnership, Tel-Aviv (IL)

(72) Inventors: Ariel Raz, Kfar Vradim (IL); David Mendlovic, Tel Aviv (IL)

(73) Assignee: Technology Innovation Momentum Fund (Israel) Limited Partnership, Tel-Aviv (IL)

( * ) Notice: Subject to any disclaimer, the term of this patent is extended or adjusted under 35 U.S.C. 154(b) by 0 days.

(21) Appl. No.: 15/746,824

(22) PCT Filed: Jul. 28, 2016

(86) PCT No.: PCT/IL2016/050827
§ 371 (c)(1),
(2) Date: Jan. 23, 2018

(87) PCT Pub. No.: WO2017/017684
PCT Pub. Date: Feb. 2, 2017

(65) Prior Publication Data
US 2018/0209850 A1 Jul. 26, 2018

Related U.S. Application Data

(60) Provisional application No. 62/198,789, filed on Jul. 30, 2015.

(51) Int. Cl.
*G01J 3/28* (2006.01)
*G01J 3/26* (2006.01)
(Continued)

(52) U.S. Cl.
CPC .......... *G01J 3/2823* (2013.01); *G01J 3/0264* (2013.01); *G01J 3/26* (2013.01); *G01J 3/2803* (2013.01);
(Continued)

(58) Field of Classification Search
CPC .......... G01J 3/26; G01J 3/2803; G01J 3/2823; G01J 3/502; G01J 2003/1226;
(Continued)

(56) References Cited

U.S. PATENT DOCUMENTS 5,834,203 A 11/1998 Katzir et al.
6,961,182 B2 11/2005 Murata
(Continued)

FOREIGN PATENT DOCUMENTS

CA 2532949 A1 2/2005
CN 1846114 A 10/2006
(Continued)

OTHER PUBLICATIONS

ISR of PCT/IL2016/050827 dated Nov. 8, 2016.
(Continued)

*Primary Examiner* — Michael A Lyons
(74) *Attorney, Agent, or Firm* — Kenealy Vaidya LLP

(57) ABSTRACT

A hyperspectral imaging system and method are presented for use in reconstruction of spectral data of an object. The system comprises: a pixel matrix of a detector; a tunable dispersive unit in front of the pixel matrix; and a control system. The control system comprises: a controller for tuning the dispersive unit during n image acquisition sessions to provide n different partially overlapping spectral transmission profiles of the dispersive unit; and a control unit which is in data communication with the detector and is configured and operable for processing n image data pieces generated by the pixel matrix in said n image acquisition
(Continued)

sessions respectively, each being indicative of a spectral image detected by the pixel matrix and corresponding to the different spectral transmission profile of the dispersive unit, and determining the reconstructed spectral data of the object.

16 Claims, 3 Drawing Sheets

(51) Int. Cl.
| | | |
|---|---|---|
| *G01J 3/02* | (2006.01) | |
| *G01J 3/50* | (2006.01) | |
| *G16H 30/20* | (2018.01) | |
| *G16H 40/63* | (2018.01) | |
| *G01J 3/12* | (2006.01) | |

(52) U.S. Cl.
CPC .............. *G01J 3/502* (2013.01); *G16H 30/20* (2018.01); *G16H 40/63* (2018.01); *G01J 2003/1247* (2013.01); *G01J 2003/2813* (2013.01); *G01J 2003/2826* (2013.01)

(58) Field of Classification Search
CPC ....... G01J 2003/1247; G01J 2003/2813; G01J 2003/2826
See application file for complete search history.

(56) References Cited

U.S. PATENT DOCUMENTS

| | | | |
|---|---|---|---|
| 7,177,505 B2 | 2/2007 | Willcox | |
| 7,554,667 B1 | 6/2009 | Kampe | |
| 7,936,056 B2 | 5/2011 | Hatakeyama | |
| 8,164,757 B2 | 4/2012 | Yamanoi et al. | |
| 8,305,575 B1* | 11/2012 | Goldstein | G01J 3/021 |
| | | | 356/326 |
| 8,384,905 B2 | 2/2013 | Wu | |
| 2002/0044575 A1 | 4/2002 | May | |
| 2004/0149915 A1 | 8/2004 | Goncalves | |
| 2005/0030545 A1* | 2/2005 | Tuschel | G01J 3/02 |
| | | | 356/454 |
| 2007/0146700 A1* | 6/2007 | Kowarz | G01J 3/02 |
| | | | 356/310 |
| 2008/0144001 A1 | 6/2008 | Heeg et al. | |
| 2010/0021133 A1 | 1/2010 | Wonfor et al. | |
| 2010/0328659 A1* | 12/2010 | Bodkin | G01J 3/02 |
| | | | 356/326 |
| 2011/0208462 A1* | 8/2011 | Maier | G01J 3/02 |
| | | | 702/104 |
| 2012/0020681 A1 | 1/2012 | Naitoh et al. | |
| 2012/0206813 A1 | 8/2012 | Bahat et al. | |
| 2015/0136981 A1* | 5/2015 | Kester | G01N 21/3504 |
| | | | 250/330 |
| 2015/0153563 A1 | 6/2015 | Kamal et al. | |
| 2015/0332081 A1* | 11/2015 | Laforest | G06K 9/0063 |
| | | | 382/191 |

FOREIGN PATENT DOCUMENTS

| | | |
|---|---|---|
| CN | 102053361 | 5/2011 |
| CN | 102053361 A | 5/2011 |
| CN | 103048781 | 4/2013 |
| CN | 103048781 A | 4/2013 |
| DE | 29824467 U1 | 3/2001 |
| WO | WO2016071909 A1 | 5/2016 |
| WO | WO2017009850 A1 | 1/2017 |

OTHER PUBLICATIONS

ISR of PCT/IL2016/050772 dated Oct. 9, 2016.
Weber, J. R., Durkin, A. J., Tromberg, B. J., Cuccia, D. J., Johnson, W. R., Wilson, D. W., . . . & Binder, D. K. (2011). Multispectral imaging of tissue absorption and scattering using spatial frequency domain imaging and a computed-tomography imaging spectrometer. Journal of biomedical optics, 16(1), 011015.
Murakami, Y., Yamaguchi, M., & Ohyama, N. (2012). Hybrid-resolution multispectral imaging using color filter array. Optics express, 20(7), 7173-7183.
Stern, Adrian. "Compressed imaging system with linear sensors." Optics letters 32.21 (2007): 3077-3079.
Wagadarikar, Ashwin, et al. "Single disperser design for coded aperture snapshot spectral imaging." Applied optics 47.10 (2008): B44-B51.
Golub, Michael A., et al. "Spectral multiplexing method for digital snapshot spectral imaging." Applied optics 48.8 (2009): 1520-1526.
Wang, Xingbo, et al. "Multispectral imaging: narrow or wide band filters?." JAIC—Journal of the International Colour Association 12 (2014).
Shrestha, Raju, and Jon Yngve Hardeberg. "Evaluation and comparison of multispectral imaging systems." Color and Imaging Conference. vol. 2014. No. 2014. Society for Imaging Science and Technology, 2014.

* cited by examiner

SPECTRAL IMAGING METHOD AND SYSTEM

TECHNOLOGICAL FIELD AND BACKGROUND

The present invention is in the field of imaging techniques, and relates to a method and system for spectral imaging.

Spectral imaging is aimed at providing at least some spectral information about an object at every location in an image plane. Various spectral imaging techniques have been developed, including multispectral imaging, hyperspectral imaging, full spectral imaging, imaging spectroscopy or chemical imaging. Spectral images are often represented as an image cube, a type of data cube.

Multispectral (MS) and hyperspectral (HS) cubes could be acquired in many ways. Some systems (utilizing whiskbroom, pushbroom and tunable filters for realizing HS imagers), rely on multiple acquisitions of 1D or 2D subsets of the 3D HS cube followed by simple reconstruction. Some other systems include polychromatic sensors that trade-off resolution with spectral information (similar to the Bayer CFA) and require spatio-spectral reconstruction algorithms [Y. Monno, M. Tanaka and M. Okutomi Proceedings of IS&T/SPIE Electronic Imaging (EI2012), Digital Photography VIII, Vol. 8299, pp. 829900-1-7, January, 2012; Y. Murakami, M. Yamaguchi, and N. Ohyama, "Hybrid-resolution multispectral imaging using color filter array," Opt. Express 20, 7173-7183 (2012)].

Recently, several HS snapshot acquisition techniques have been developed. Some of them are based on compressed sensing in which the HS image is assumed to be sparse, and an additional optical element is used within the imaging system, to compress the data. Such techniques are described in the following publications: A. Stern, "Compressed imaging system with linear sensors," Opt. Lett. 32, 3077-3079 (2007); A. Wagadarikar, R. John, R. Willett, and D. Brady, "Single disperser design for coded aperture snapshot spectral imaging," Appl. Opt. 47, B44-B51 (2008); C. Li, T. Sun, K. F. Kelly and Y. Zhang. A compressive sensing and unmixing scheme for hyperspectral data processing. IEEE_J_IP 21(3), pp. 1200-1210. 2012; M. A. Golub, M. Nathan, A. Averbuch, E. Lavi, V. A. Zheludev, and A. Schclar, "Spectral multiplexing method for digital snapshot spectral imaging," Appl. Opt. 48, 1520-1526 (2009).

However, these techniques require prior knowledge of the scene being imaged, and also typically suffer from low light efficiency, and systems implementing such techniques are rather complex.

As for the integral field spectroscopic systems, the common underlying principle of these systems is similar to light field cameras in the sense that the spectral information is traded-off with spatial resolution. Thus, a number of spectral bands in the detected light is equal to the resolution degradation ratio. Integral field hyperspectral imaging techniques, such as lenslet array, fibre array, image slicer and microslicer, all exhibit this behavior. Yet another known solution concerns the use of a 2D grating that diverges incident light according to the grating' diffraction order to form multiple, multispectral sub-images on the sensor; this is followed by reconstruction algorithms. This method allows fast hyperspectral cube acquisition, but the resultant image suffers from low spatial resolution; also the required setup could not be integrated in common cameras.

General Description

The present invention provides a novel technique for hyperspectral imaging that enables to acquire a complete hyperspectral cube of arbitrary scene. The invention provides for acquiring a hyperspectral cube with full spatial resolution and spectral resolution. This technique needs neither any preliminary information of the scene nor additional assumptions.

A hyperspectral imaging system of the invention includes a wide spectral filter/etalon, e.g. a clear aperture Fabry-Perot etalon with wide transmission peak, placed in front of a pixel matrix of a detector, i.e. upstream of the pixel matrix with respect to the input light propagation direction. The system operates in a "multiple-exposure" mode to acquire multiple frames of the scene, while using multiple different, partially overlapping transmission curves of the etalon. More specifically, the system operates to acquire a set of frames, each with a different transmission function of the etalon, i.e. slightly displaced transmission peak of the etalon. The transmission profiles are wide to capture more light and consequently improve the signal to noise ratio. Thus, each frame is acquired with a pre-determined weighted sum of wavelengths, and the spectral profiles of each two exposures (frames) may significantly overlap. Following the acquisition, spectral reconstruction algorithms are applied to recover the spectrum of the image. In general, the number of spectral bands is equal to the number of exposures.

Thus, the present invention provides for acquiring a complete hyperspectral cube of arbitrary scene with full spatial and spectral resolutions, while having a simple construction of standard imaging system, additionally equipped with a tunable dispersive element (spectral filter) with broad spectral transmission profiles that allows acquiring within each frame a weighted sum of wavelengths. The hyperspectral imaging system of the invention could be integrated within both color (Bayer) and monochrome image sensors. The clear aperture Fabry-Perot etalon may also be used for standard color imaging, thus enabling a dual-purpose imaging system (standard color+hyperspectral). The system has improved noise performance, since each frame is acquired with reduced noise content.

The approach of the invention is general and may fit multiple imaging scenarios, including UV/VIS/NIR; and is not sensor dependent. The imaging system of the invention may be integrated in industrial cameras, surveillance cameras, medical devices, quality control equipment, spectrometry systems for inspecting chemical compounds and biological tissues.

The present invention takes advantage of the hyperspectral imaging technique described in U.S. patent application No. 62/075,972, assigned to the assignee of the present application, and incorporated herein by reference. This technique is based on applying angular coding on an input light field while creating an optical image thereof, thus providing angular multiplexing of hyperspectral image data (hyperspectral cube). This technique is effectively operable for objects of a size that can be imaged on at least N pixels of the pixel array to allow reconstruction of N spectral bands.

The technique of the present invention provides for effective spectrum reconstruction of very small objects up to single-pixel objects. To this end, the invention utilizes multi-exposure approach with different transmission functions of the wide spectral etalon.

The tunable etalon is configured for tunability over a relatively wide spectral range, and also preferably with sufficient Free Spectral Range (FSR). Furthermore, in order to enable generation of accurate color images, the etalon is preferably configured with low finesse (namely sufficiently wide spectral transmission peak). This, on the one hand, provides for creating images with accurate (e.g. faithful) colors, and, on the other hand, allows sufficient light to pass to the sensor (pixel matrix).

The etalon typically includes a pair of substantially parallel, generally reflective surfaces, spaced from one another by a gap (optical distance). Generally, the transmission function T of such etalon is a function of wavelength $\lambda$, transmission of the two surfaces, and the value of gap between these surfaces. For the etalon formed by given reflective surfaces (i.e. given transmission(s) thereof), the etalon's transmission is a function of wavelength and gap, $T(\lambda, gap)$. Thus, by controllably varying the gap between the reflective surface to provide a sequence of n different gap values during image acquisitions of n frames (n exposures), respectively, different n transmission functions of the etalon are applied to the input light field which differently affect detection of light components of n wavelengths $\lambda_1, \ldots \lambda_N$ by the pixel matrix of the detector. This allows reconstruction of the spectrum of the object by processing the image data of n frames.

Thus, according to one broad aspect of the invention, there is provided a hyperspectral imaging system for use in reconstructing spectral data of an object, the system comprising:

a pixel matrix of a detector;

a dispersive unit in front of the pixel matrix; and a control system comprising: a controller for tuning the dispersive unit to provide n different partially overlapping spectral transmission profiles thereof during n image acquisition sessions; and a control unit in data communication with the detector and being configured and operable for processing n image data pieces generated by the pixel matrix in said n image acquisition sessions respectively, each being indicative of a spectral image detected by the pixel matrix and corresponding to the different spectral transmission profile of the dispersive unit; and determining the reconstructed spectral data of the object.

The transmission profile of the dispersive unit is a function of wavelength and a tunable parameter (e.g. gap) of the dispersive unit. The plurality of the image data pieces is a function of the plurality of the transmission profiles of the dispersive unit and the spectrum of the object to be determined.

The dispersive unit comprises a spectral filter, e.g. an etalon, configured with a wide spectral range. Passage of light through the dispersive unit provides wavelength multiplexing of image data at the pixel matrix, such that detected light intensity at the pixel corresponds to the spectral data of the image multiplexed with the transmittance function (dispersion profile/pattern) of the dispersive unit.

The controller, configured and operable for tuning the dispersive unit to sequentially produce the different transmittance profiles for acquiring the sequential frames of the object, may be integrated with the control unit associated with the detector or may be a separate utility.

According to another aspect, the invention provides an imaging method for use in reconstructing spectral data of an object. The method comprises: sequentially acquiring a plurality of n image frames, by performing n imaging sessions of the object onto a pixel matrix of a detector, while sequentially applying to the light being imaged n predetermined dispersion profiles being different from one another and partially overlapping, thereby obtaining n image data pieces indicative of n different spectral images of the object; and processing said n image data pieces utilizing the data about the predetermined n dispersion profiles, and reconstructing n spectral bands of the object being imaged.

The application of the dispersion profile to the light is achieved by interacting the light with a dispersive pattern. The image data piece is a function of the corresponding dispersive profile and a spectrum of the object to be determined.

The invention in its further aspect provides a control unit for reconstructing spectral data of an object. The control unit is configured for receiving and processing input image data (either directly from an imaging system or from a storage device). The received image data comprises data indicative of n image data pieces corresponding to n spectral images obtained by a pixel matrix, where each of the n spectral images is formed by light coded by a different dispersive profile. The control unit comprises an analyzer configured and operable for utilizing data indicative of the n dispersive profiles in association with the respective n image data pieces and determining the spectral data of the object.

BRIEF DESCRIPTION OF THE DRAWINGS

In order to better understand the subject matter that is disclosed herein and to exemplify how it may be carried out in practice, embodiments will now be described, by way of non-limiting examples only, with reference to the accompanying drawings, in which.

DETAILED DESCRIPTION OF EMBODIMENTS

Figure 1:
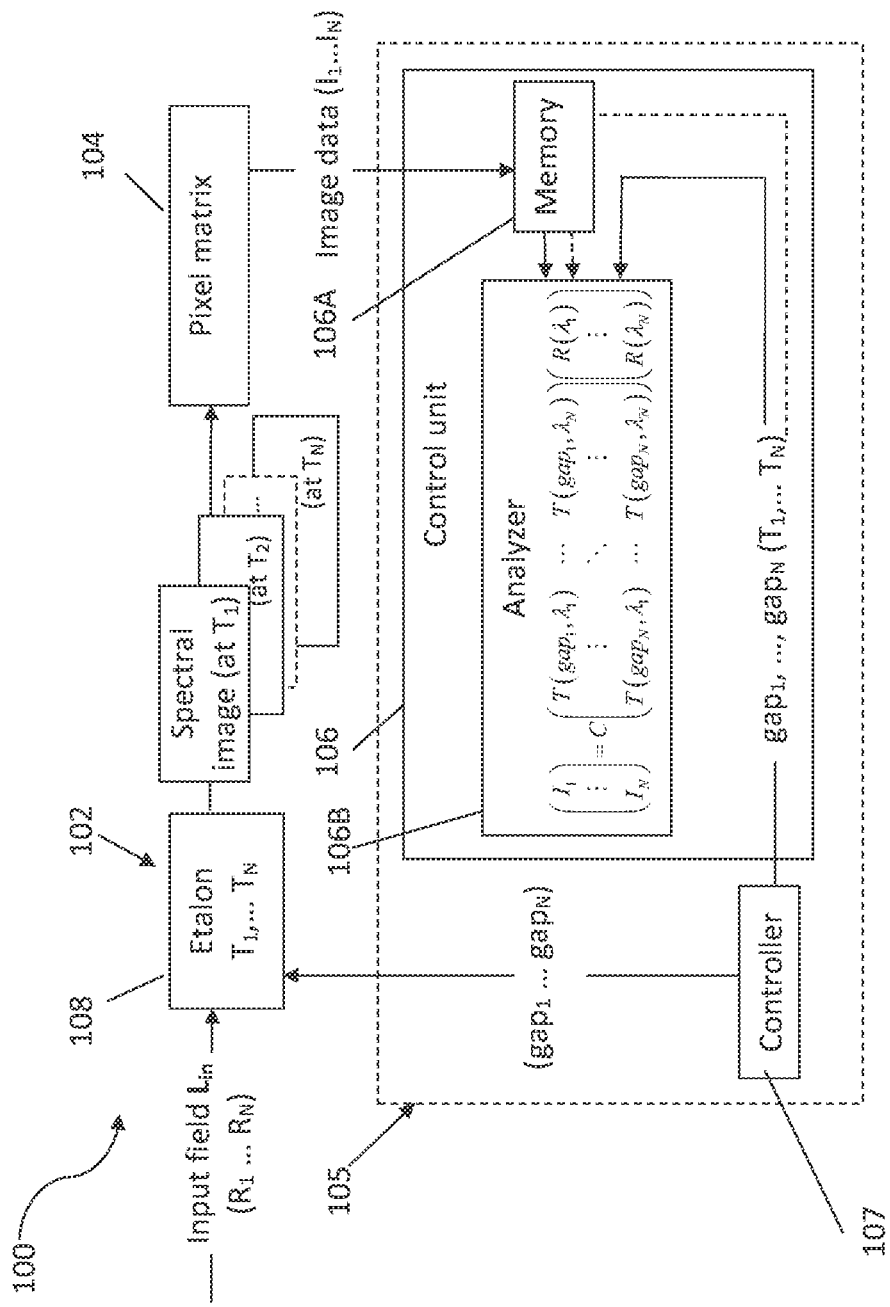
FIG. 1 is a block diagram of a hyperspectral imaging system of the present invention.

Reference is made to FIG. 1 illustrating, by way of a block diagram, a hyperspectral imaging system 100 of the invention. The imaging system 100 includes an optical unit 102 for locating in front of (upstream of) an imaging plane IP defined by a pixel matrix unit 104 of a detector, and a control system 105. The control system 105 includes a control unit 106 configured for data communication with a readout circuit of the pixel matrix 104 for receiving image data therefrom and processing the received data. The control unit 106 may be integral with the pixel matrix unit 104, e.g. may be a software module of the readout circuit of the pixel matrix unit 104.

The optical unit 102 includes a tunable dispersive unit/element being a wide spectral filter 108. For example, a clear aperture Fabry-Perot etalon with wide transmission peak can be used.

The control unit 106 includes inter alia data input and output utilities (not shown), a memory module 106A, an analyzer module 106B adapted for analyzing the image data from the pixel matrix unit 104. This will be described more specifically further below.

Also provided in the control system 105 is a controller 107, which is configured for controlling the tuning of the etalon 108 and providing data about the variation of the tunable parameter. The controller may be part of the control unit 106, or may be a separate module, or may be part of the etalon 108. The tuning of the etalon is aimed at controllably varying its spectral transmission profile (transmission function), i.e. changing the dispersive pattern of light passing therethrough. In case of the Fabry-Perot type etalon, the tunable parameter of the etalon 108 is a gap between its reflective surfaces. The controller 107 operates the tuning procedure and provides data about the different values of the tunable parameter, e.g. $gap_1, \ldots gap_N$, or provides data about the corresponding transmission functions of the etalon, $T_1, \ldots T_N$.

Figure 2:
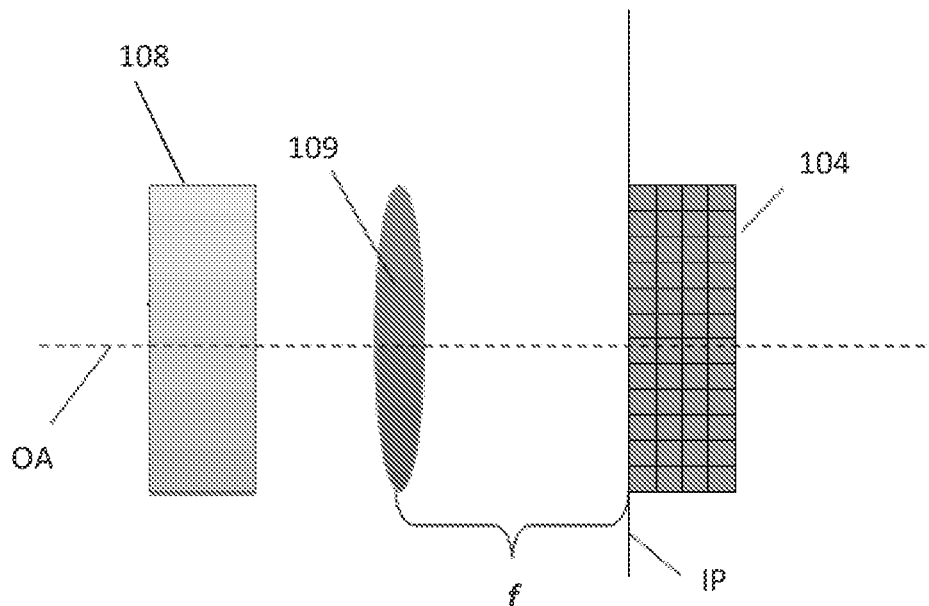
FIG. 2 more specifically illustrates the light propagation scheme in the system of the invention.

As exemplified in FIG. 2, the etalon 108 is preferably located in front of an imaging lens module 109 of the detector being spaced-apart therefrom along an optical axis OA. The pixel matrix 104 is located in the imaging plane IP which is typically located in a back focal plane of the lens module 109.

Figure 3:
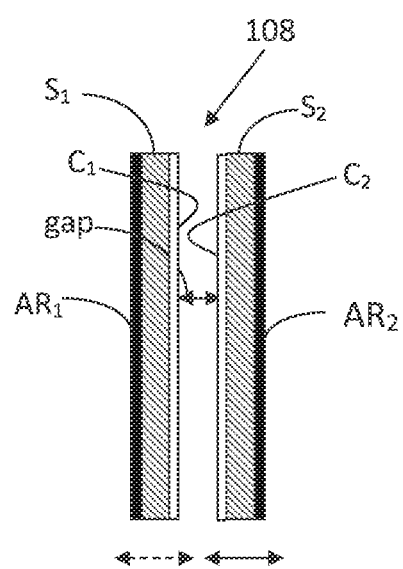
FIG. 3 schematically illustrates a Fabry-Perot etalon suitable to be used in the system of the present invention.

FIG. 3 more specifically exemplifies the configuration of etalon 108 tunable to provide various spectral transmission curves. The tunable etalon 108 is preferably sufficiently thin to fit in the optical path of a camera. The tunable etalon 108 of this example is configured as a clear aperture Fabry-Perot etalon formed by two reflectors (reflective surfaces) $S_1$ and $S_2$. The reflectors $S_1$ and $S_2$ are spaced apart by a gap (etalon-spacing), which is variable/tunable, by moving at least one of the surfaces with respect to the other, to vary the spectral transmission profile of the etalon. As shown in the figure, the inner surfaces of the reflectors $S_1$ and $S_2$ may be provided with coatings $C_1$ and $C_2$ having high refractive index, to thereby provide for relatively wide spectral transmission peak of the etalon, and the outer surface of at least one of the mirrors $S_1$ and $S_2$ may be provided with anti-reflective coating—two such anti-reflective coatings $AR_1$ and $AR_2$ on the mirrors $S_1$ and $S_2$ are shown in this example.

At least one of the reflective surfaces $S_1$ and $S_2$ of the etalon 108 is mounted on/associated with actuator(s) providing for controlling the gap between the reflective surfaces. The actuator(s) may include piezoelectric actuator(s) and/or MEMS actuator, such as electrostatic MEMS actuator. Alternatively or additionally the etalon 108 may include electro-optical media placed in the space between the reflective surfaces $S_1$ and $S_2$. Such electro optical media is configured and operable for providing control over the optical distance between the reflective surfaces.

Turning back to FIG. 1, the imaging system 100 operates in a multiple-exposure mode, namely acquires a set/sequence of frames, each being a different spectral image of a region of interest (as a result of input light interaction with different dispersive pattern). During each exposure or imaging session (each frame acquisition), the input light field Lin, propagating from the region of interest, passes through the etalon 108 having a certain transmission profile (i.e. spectral position of the transmission peak), defined by a certain value of the gap being different from that of the other exposures/imaging sessions. A resulting spectral image is detected by the pixel matrix. A set of frames is acquired, each with a slightly displaced transmission peak. Thus, during n exposures performed with n different partially overlapping transmission profiles of the etalon, $T_1, \ldots T_N$, achieved by setting n values of the gap, n different spectral images are detected. The transmission profiles are wide to capture more light and consequently improve the signal to noise ratio.

Figure 4:
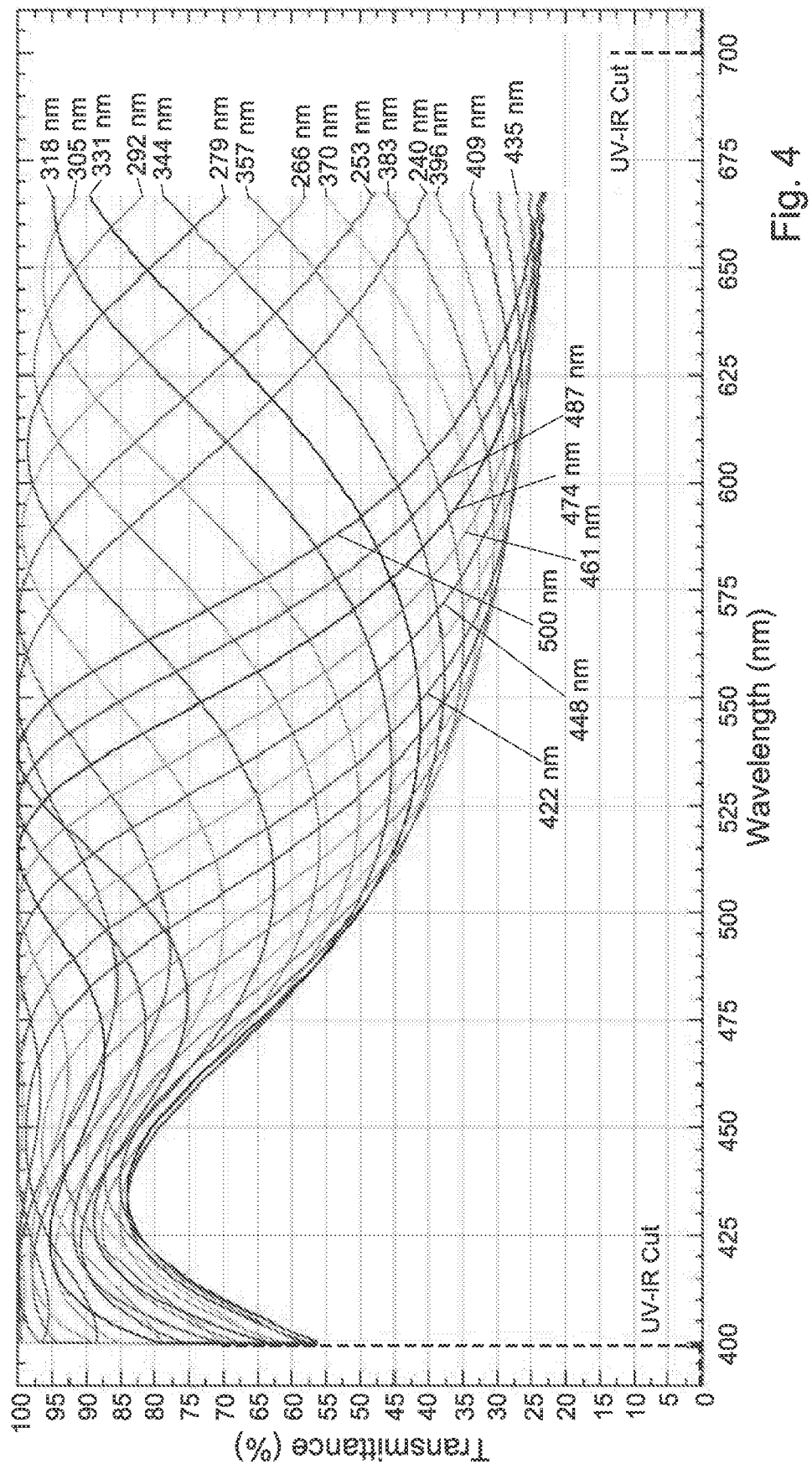
FIG. 4 illustrates simulation results for transmission curves of the etalon as a function of wavelength and a gap between the reflective surfaces of the etalon.

FIG. 4 illustrates simulation results for transmission curves of the etalon as a function of wavelength and a gap between the reflective surfaces of the etalon. In this simulation, a wide tunable spectral filter (Fabry-Perot etalon) is considered providing the transmission curves within the spectral range of 400 nm-700 nm.

Typically, in an imaging system, each pixel measures the overall intensity of light rays incident on said pixel at different angles. The light passage through the etalon 108 provides that each wavelength component of the input light is differently affected by the transmission profile of the etalon. Thus, each pixel in the pixel matrix 104 measures the integrated intensity of multiple weighted modified spectra. Accordingly, each frame is acquired with a pre-determined weighted sum of wavelengths. The spectral profiles of each two exposures (frames) may significantly overlap. The number of the detected spectral bands is equal to the number of exposures.

The control unit 106 receives the output of the pixel matrix in the form of n image data pieces $I_1, \ldots I_N$, which are indicative of the spectral images detected during the n frames' acquisition with n different transmission profiles of the etalon defined by n different gaps. This image data pieces may be stored in the memory 106A. The variation of the gap values is managed by the controller 107, and the corresponding transmission profiles of the etalon are thus known. The values of gaps and/or corresponding transmission profiles may also be stored in the memory.

The analyzer 106B utilizes the transmission profiles' data for processing the image data $I_1, \ldots I_N$ for detecting/reconstructing the spectrum of the object being imaged. The image data can be written as:

$$\begin{pmatrix} I_1 \\ \vdots \\ I_N \end{pmatrix} = C \begin{pmatrix} T(gap_1, \lambda_1) & \ldots & T(gap_1, \lambda_N) \\ \vdots & \ddots & \vdots \\ T(gap_N, \lambda_1) & \ldots & T(gap_N, \lambda_N) \end{pmatrix} \begin{pmatrix} R(\lambda_1) \\ \vdots \\ R(\lambda_N) \end{pmatrix}$$

wherein R is the spectral reflectance from the object with N spectral bands, and I is the pixel intensity per exposure, T is the transmission of the filter (etalon) being a function of gap and wavelength, and C is a normalization factor.

The reflectance vector of the object could thus be reconstructed by:

$$\begin{pmatrix} R(\lambda_1) \\ \vdots \\ R(\lambda_N) \end{pmatrix} = \frac{1}{C} \begin{pmatrix} T(gap_1, \lambda_1) & \ldots & T(gap_1, \lambda_N) \\ \vdots & \ddots & \vdots \\ T(gap_N, \lambda_1) & \ldots & T(gap_N, \lambda_N) \end{pmatrix}^{-1} \begin{pmatrix} I_1 \\ \vdots \\ I_N \end{pmatrix}$$

In case the number of exposures exceeds the required spectral resolution, an error minimization may be applied such as least mean squares. Alternatively, the spectral resolution (spectral bands) may be increased up to the number of exposures.

As indicated above, the etalon is preferably tunable within a wide spectral range. The tuning is achieved by varying the gap between the reflectors $S_1$ and $S_2$. Such a wide spectral range tunable etalon may require a high aspect ratio between the width and gap between the reflectors, and also the gap is to be adjustable to be variable to very close proximity between the reflectors (e.g. a few tens of nanometers). Also, as indicated above, the gap variation can be achieved by associating at least one of the reflectors with actuator(s) operable to controllably move at least one of the reflectors with respect to the other, e.g. MEMs-based actuator(s). An example of a tunable MEMS-based etalon suitable to be used in the imaging system of the present invention is described in U.S. patent application No. 62/192,658, assigned to the assignee of the present application and incorporated herein by reference in its entirety.

Thus, the present invention provides novel, simple and effective hyperspectral imaging technique enabling reconstruction of the spectrum of an object/scene. The invention provides for acquiring a hyperspectral cube with full spatial resolution and spectral resolution, without any preliminary information about the object/scene being imaged.

We claim:

1. A hyperspectral imaging system for use in reconstructing spectral data of an object, the system comprising:
    a pixel matrix of a detector;
    a dispersive unit in front of the pixel matrix, wherein the dispersive unit comprises a spectral filter; and
    a control system comprising:
        a controller for tuning the dispersive unit during n image acquisition sessions to provide n different spectral transmission profiles of the dispersive unit; wherein n is an integer that exceeds one; wherein the different spectral transmission profiles partially overlap; and
        a control unit in data communication with the detector and being
            configured and operable for processing n image data pieces generated by the pixel matrix in said n image acquisition sessions respectively, each being indicative of a spectral image detected by the pixel matrix and corresponding to the different spectral transmission profiles of the dispersive unit, and determining, based on the different spectral transmission profiles of the dispersive unit, a reconstructed spectral data of the object.

2. The imaging system of claim 1, wherein the spectral filter is an etalon configured with a wide spectral range.

3. The imaging system of claim 2, wherein the dispersive unit is configured as a clear aperture Fabry-Perot etalon.

4. The imaging system of claim 3, wherein the imaging system is being configured and operable as a dual-purpose imaging system, selectively operating the dispersive unit in a standard color imaging mode during which a single image acquisitions is performed and in a hyperspectral imaging mode during which the n image acquisition sessions are performed.

5. The imaging system of claim 2, wherein the control unit is configured and operable for processing the n image data pieces and determining the reconstructed spectral data of the object, utilizing the following relation between the n image data pieces h, ... TN and n spectral bands R(A−1) ... R(AN) of the object:

$$\begin{pmatrix} I_1 \\ \vdots \\ I_N \end{pmatrix} = C \begin{pmatrix} T(gap_1, \lambda_1) & \cdots & T(gap_1, \lambda_N) \\ \vdots & & \vdots \\ T(gap_N, \lambda_1) & \cdots & T(gap_N, \lambda_N) \end{pmatrix} \begin{pmatrix} R(\lambda_1) \\ \vdots \\ R(\lambda_N) \end{pmatrix}$$

wherein T is a spectral transmission profile of the dispersion unit being a function of a gap between reflective surfaces of the etalon and wavelength A, and C is a normalization factor.

6. The imaging system of claim 1, wherein each one of the n different transmission profiles of the dispersive unit is a function of wavelengths and a tunable parameter of the dispersive unit.

7. The imaging system of claim 6, wherein the plurality of the image data pieces is a function of the plurality of the n different transmission profiles of the dispersive unit and the reconstructed spectral data of the object.

8. The imaging system of claim 1, wherein during each image acquisition session of then image acquisition sessions, a passage of light through the dispersive unit provides wavelength multiplexing of image data at the pixel matrix, such that for each pixel of the pixel matrix a detected light intensity at the pixel corresponds to the spectral data of the image multiplexed with a transmittance function of the dispersive unit applied during the image acquisition session.

9. The imaging system of claim 1, wherein the detector is configured as a monochromatic or color detector.

10. A hyperspectral imaging method for use in reconstructing spectral data of an object, the method comprising:
    sequentially acquiring a plurality of n image frames, by performing n imaging sessions of the object onto a pixel matrix of a detector, while sequentially applying, by a dispersive unit that comprises a spectral filter, to light being imaged on the dispersive unit, n different dispersion profiles that are different from one another and partially overlap, thereby obtaining n image data pieces indicative of n different spectral images of the object, wherein n is an integer that exceeds one; and
    processing said n image data pieces utilizing data about the n different n dispersion profiles, and reconstructing n spectral bands of the object being imaged.

11. The method of claim 10, wherein said applying of then different dispersion profiles comprises interacting the light with a dispersive pattern.

12. The method of claim 10, wherein data indicative of the n image data pieces is a function of the n different dispersive profiles and a spectrum of the object.

13. The method of claim 10 wherein each one of different dispersive profiles of the dispersive unit is a function of wavelengths and a tunable parameter of the dispersive unit.

14. The method of claim 10 wherein the determining of the reconstructed spectral data of the object, comprises utilizing the following relation between the n image data pieces h, ... TN and n spectral bands R(A−1) ... R(AN) of the object:

$$\begin{pmatrix} I_1 \\ \vdots \\ I_N \end{pmatrix} = C \begin{pmatrix} T(gap_1, \lambda_1) & \cdots & T(gap_1, \lambda_N) \\ \vdots & & \vdots \\ T(gap_N, \lambda_1) & \cdots & T(gap_N, \lambda_N) \end{pmatrix} \begin{pmatrix} R(\lambda_1) \\ \vdots \\ R(\lambda_N) \end{pmatrix}$$

wherein T is a spectral transmission profile of the dispersion unit being a function of a gap between reflective surfaces of the etalon and wavelength A, and C is a normalization factor.

15. A control unit for reconstructing spectral data of an object,
    the control unit being configured for receiving input data comprising data indicative of n image data pieces corresponding to n spectral images obtained by a pixel matrix, each of said n spectral images being coded by a dispersive unit that comprises a tunable filter while applying a different dispersive profile out of n different dispersive profiles, wherein n is an integer that exceeds one; and
    wherein the control unit comprising an analyzer configured and operable for utilizing data indicative of the n different dispersive profiles in association with the respective n image data pieces and determining the spectral data of the object.

16. The control unit of claim 15, configured and operable for processing the n image data pieces and determining the reconstructed spectral data of the object, utilizing the following relation between the n image data pieces '1, ... TN and n spectral bands
R(li.1) ... R(li.N) of the object:

$$\begin{pmatrix} I_1 \\ \vdots \\ I_N \end{pmatrix} = C \begin{pmatrix} T(gap_1, \lambda_1) & T(gap_1, \lambda_N) \\ \vdots & \vdots \\ T(gap_N, \lambda_1) & T(gap_N, \lambda_N) \end{pmatrix} \begin{pmatrix} R(\lambda_1) \\ \vdots \\ R(\lambda_N) \end{pmatrix}$$

wherein the tunable filter is an etalon and wherein T is a dispersive profile as that is a function of a gap between reflective surfaces of the etalon, and wavelength A, and C is a normalization factor and wavelength A, and C is a normalization factor.

* * * * *